United States Patent [19]

Huang et al.

[11] Patent Number: 4,465,774
[45] Date of Patent: Aug. 14, 1984

[54] STANDARD OR CONTROL MATERIAL FOR GLYSOCYLATED OR TOTAL HEMOGLOBIN DETERMINATION

[75] Inventors: John J. Huang, San Mateo; Jung-Shou Chen, Foster City; Louis M. Mezei, Fremont, all of Calif.

[73] Assignee: Sherwood Medical Company, St. Louis, Mo.

[21] Appl. No.: 283,940

[22] Filed: Jul. 16, 1981

[51] Int. Cl.³ .................... C09K 3/00; G01N 33/72; G01N 33/96
[52] U.S. Cl. ............................. 436/15; 436/13; 436/16; 436/17; 436/66; 436/67; 424/101; 435/2; 435/188
[58] Field of Search .................. 436/13, 15, 17, 16, 436/66, 67, 71; 424/101; 435/2, 188

[56] References Cited

U.S. PATENT DOCUMENTS

| | | | |
|---|---|---|---|
| 3,876,375 | 4/1975 | Maurukas | 436/15 |
| 3,991,181 | 11/1976 | Doczi | 436/15 |
| 4,001,401 | 1/1977 | Bonsen | 436/15 |
| 4,011,045 | 3/1977 | Bonderman | 436/13 |
| 4,040,785 | 8/1977 | Kim et al. | 436/16 |
| 4,045,176 | 8/1977 | Proksch et al. | 436/13 |
| 4,056,468 | 11/1977 | Breiter et al. | 436/13 |
| 4,099,917 | 7/1978 | Kim | 436/10 |
| 4,102,810 | 7/1978 | Armstrong | 436/17 |
| 4,189,401 | 2/1980 | Louderback | 436/11 |
| 4,200,435 | 4/1980 | Stroupe et al. | 436/15 |
| 4,215,994 | 8/1980 | Kodras | 210/21 |
| 4,216,117 | 8/1980 | Proksch et al. | 436/13 |
| 4,260,516 | 4/1981 | Moore | 436/15 |

FOREIGN PATENT DOCUMENTS

| | | | |
|---|---|---|---|
| 7603767 | 1/1977 | Brazil | 436/15 |
| 7608751 | 10/1977 | France | 436/16 |

OTHER PUBLICATIONS

Labrude, P., et al; Clin. Chem., vol. 26, No. 13, pp. 1926–1927 (1980).
Bonderman, D. P., Clin. Chem., vol. 26, No. 13, pp. 1927 (1980).
Bonderman, D. P., et al; Clin. Chem., vol. 26, No. 2, pp. 305–308 (1980).
Delgado, M. L., et al., Clin. Chem., vol. 27, No. 2, pp. 358–359 (1981).
C. A., vol. 93, 236048t (1980).
Labrude, P., et al., J. Pharm. Belg., vol. 31, p. 191 (1976).
Labrude, P., et al., Ann. Pharm. Fr., vol. 34, p. 143 (1976).

Primary Examiner—Teddy S. Gron
Attorney, Agent, or Firm—Stanley N. Garber; Gregory E. Upchurch; William R. O'Meara

[57] ABSTRACT

A control material for use in the determination of glycosylated and total hemoglobin, and a method of preparing the same, are disclosed. The control is prepared by the steps of hemolyzing red blood cells, preferably in the presence of a detergent, followed by removal of stroma and lipids from the hemoglobin with an organic solvent such as toluene in the presence of a polyhydroxy compound such as sucrose. A hemoglobin-rich fraction is separated from the resulting mixture and dialyzed against a solution of a polyhydroxy compound. The dialysate may be lyophilized to provide a stable, dry product suitable for reconstitution.

18 Claims, 8 Drawing Figures

STANDARD OR CONTROL MATERIAL FOR GLYSOCYLATED OR TOTAL HEMOGLOBIN DETERMINATION

BACKGROUND OF THE INVENTION

1. Field of the Invention

This invention relates generally to a control material useful in hemoglobin determination and, more specifically, this invention relates to a method for preparing a stable, nonturbid hemoglobin control material which comprises oxyhemoglobin with only traces of methemoglobin.

2. Description of the Prior Art

The determination of both total hemoglobin and glycosylated hemoglobin, specifically hemoglobin Alc (HbAlc), which is also referred to as glycosylated oxyhemoglobin, is recognized as clinically important in the diagnosis and monitoring of control in diabetic patients. The concentration of hemoglobin Alc is recognized as being directed related to time-averaged blood glucose levels and is correlated with various stages of metabolic control in diabetic patients.

Normal, nondiabetic patients have a HbAlc level of between about 4–8% of total hemoglobin, while the HbAlc level in diabetic patients may range up to about 20% of total hemoglobin. Hypoglycemic patients correspondingly have a HbAlc level below about 3% of total hemoglobin.

Various clinical methods have been developed to provide practical means for assessing the HbAlc level in a sample of a patient's blood. Such methods include both electrophoretic and chromatographic techniques.

In both electrophoretic and chromatographic methods, standards and control materials having known glycosylated hemoglobin concentrations are necessary in order to assure day-to-day consistency of test results and to provide a reference for calibration of equipment.

One prior chromatographic procedure for determining glycosylated hemoglobin levels is a microcolumn chromatography method embodied in a test kit sold by Isolab, Inc. of Akron, Ohio under the trademark "Quik-Sep ® Fast Hemoglobin ™ " system. In the Isolab Quik-Sep ® system, both total and glycosylated hemoglobin are determined. In this procedure, whole blood is hemolyzed and placed on a disposable column containing an ion exchange resin. A so-called "fast" hemoglobin fraction is eluted from the column with a first buffer solution, and the remaining ("other") hemoglobins are eluted with a second buffer solution. The "fast" hemoglobin consists of glycosylated hemoglobins. After dilution of the second fraction with water, the optical density of each eluate fraction is determined with a standard spectrophotometer, and compared with the optical density of a standard solution having a known amount of hemoglobin.

Another commercially available column chromatography test method for determining glycosylated hemoglobin is sold by BioRad Laboratories, Richmond, Calif. under the trademark "BioRad Hemoglobin Alc Column Test".

The accuracies of the microcolumn chromatography test procedures referred to above are subject to day-to-day variations due to changes in temperature, or changes in the pH of the ion exchange resin. Therefore, it is important that a reliable standard or control material be available to provide a reference for calibration of the column.

Prior hemoglobin control materials, some of which are provided in lyophilized form, have typically contained undesirably high amounts of cyanomethemoglobin, methemoglobin or cyanohemoglobin, the presence of which adversely affects the accuracy of glycosylated hemoglobin determination, since these forms of hemoglobin travel through an ion exchange column at different rates than does glycosylated hemoglobin, and their absorption spectra differ from that of "native" hemoglobin.

Furthermore, prior liquid or reconstituted dry control materials are generally turbid, contain particulate matter, and/or have low shelf lives. Turbidity is generally caused by the presence of lipids or cell stroma. Also, prior controls sometimes contain preservatives in order to enhance shelf life. Such preservatives are generally undesirable because they bind with or dissociate the hemoglobin molecule, or otherwise adversely affect hemoglobin present in the control material.

As a result, prior hemoglobin controls and standards often contain a modified form of hemoglobin, whose absorption characteristics are dissimilar to natural hemoglobin, or which are unstable due to autooxidation.

SUMMARY OF THE INVENTION

It is an object of the invention to overcome one or more of the problems described above.

According to the present invention, a stable hemoglobin standard and control material, the hemoglobin of which consists essentially of oxyhemoglobin and which is substantially free of lipids or stroma is provided.

The control material of the invention is provided in solution form, or in lyophilized form suitable for reconstitution with water or any of various buffer solutions.

The control material of the invention is prepared by means of hemolysis of red blood cells, preferably with a detergent such as, for example, Triton ® X-100, a neutral detergent sold by Rohm and Haas Co., Independence Mall West, Philadelphia, Pa. After hemolysis, the hemolysate is mixed with toluene or another organic solvent in the presence of a polyhydroxy compound, such as sucrose, to remove lipids and stroma from the hemoglobin present in the hemolysate, and to sterilize the hemoglobin. A hemoglobin-containing fraction is separated from the resulting mixture, preferably by centrifugation, and is then dialyzed against a solution of a polyhydroxy compound to remove residual detergent and organic solvent. The dialysate's optical density is then adjusted by dilution with water and addition of a solution of the polyhydroxy compound used in dialysis so that the optical density of the dialysate approximates that of whole blood.

The dialysate is preferably lyophilized after adjustment of optical density, and is preferably, but not necessarily, stored under nonoxidizing conditions at a reduced temperature.

The resulting dry product is suitable for reconstitution with water or a suitable buffer solution and, upon reconstitution, provides a stroma-free, nonturbid, stable hemoglobin solution.

The procedure of the invention may be practiced upon normal, hyperglycemic or hypoglycemic-derived blood samples to provide control and standard materials having predetermined glycosylated hemoglobin levels.

Other objects and advantages of the invention will be apparent to those skilled in the art from the following detailed description, drawings and appended claims.

DETAILED DESCRIPTION OF THE INVENTION

According to the present invention, a stable hemoglobin control material, the hemoglobin of which consists essentially of oxyhemoglobin with only trace amounts, at most, of methemoglobin, is obtained from a sample of whole blood by separation of red blood cells from the sample, washing and hemolysis of the red blood cells, preferably with a detergent, followed by removal of lipids and stroma from the hemoglobin with toluene or another organic solvent and a polyhydroxy compound, and dialysis of the resulting hemolysate to remove residual organic solvent and detergent.

The control material can be prepared from samples of blood obtained from hypoglycemic patients, normal patients, or diabetic patients in order to provide a control material having a glycosylated hemoglobin concentration corresponding to the glycosylated hemoglobin levels of the blood of each type of patient, as desired.

The method of the invention utilizes the following generalized steps:

Red blood cells are separated from a sample of whole blood, as by centrifugation. The separated red blood cells are then washed in saline and centrifuged to separate the cells from serum, and the serum is removed from the cells, as by aspiration. The washing and centrifugation step may be repeated several times, as necessary.

The washed red blood cells are then hemolyzed, preferably in the presence of a detergent in order to liberate hemoglobin from the cells. It has been found that the use of specific types of detergents result in formation of a hemoglobin-rich hemolysate, with substantially complete destruction of intact cells.

A preferred type of detergent is an octyl phenoxypolyethoxyethanol compound sold by Rohm and Haas Co. under the trademark Triton ® X-100.

Other detergents suitable for lysing red blood cells according to this invention include cationic detergents such as cetyl trimethyl ammonium bromide, for example; anionic detergents such as sodium dodecylsulfate and sodium deoxycholate, for example; and other neutral detergents such as saponin, for example.

Although lysis with a detergent is preferred, lysis may be accomplished by other known methods, such as by freeze/thaw cycles. Lysis with water is not preferred, since water alone is a relatively inefficient lysing agent.

After lysis, lipids and stroma are separated from liberated hemoglobin in the hemolysate with a selected organic solvent in the presence of a selected first polyhydroxy compound other than glucose, and the resulting hemoglobin-rich fraction is separated from the mixture, as by centrifugation. It has been found that separation of lipids and stroma from the hemolysate with the organic solvent in the presence of the first polyhydroxy compound effectively sterilizes the hemoglobin, thus eliminating the need for a preservative which may have undesirable effects on the hemoglobin.

In addition, the organic solvent effects substantially complete lysis of residual cells, dissolves lipids, and mechanically removes debris resulting from lysis to a layer or disc which is easily separated from the hemolysate.

Typical organic solvents useful in the invention include aliphatic or aromatic compounds such as petroleum ether, heptane, hexane, ether, benzene and xylene, for example. Toluene is preferred.

A preferred first polyhydroxy compound is sucrose, although a wide variety of other polyhydroxy compounds may be used.

Suitable first polyhydroxy compounds include, but are not necessarily limited to, glycerol, ethylene glycol, propylene glycol, sorbitol, and various mono-, di-, and poly-saccharides, including both aldoses and ketoses.

Suitable mono-saccharides include mannose, fructose, sorbose and mannitol. Di-saccharides useful in the invention include sucrose, maltose and lactose. Raffinose and melizatose are two useful tri-saccharides, and Ficoll (a trademark of Pharmacia Fine Chemicals, Piscataway, N.J.) is a useful poly-saccharide.

Suitable d-aldoses include d-sibose, d-arabinose, d-xylose, d-lyxose, d-allose, d-altrose, d-gulose, d-idose, d-galactose and d-talose.

Other carbohydrates useful in the invention include dulcitol (galactilol), d-erythrose, d-fucose (d-fucopyranose), myoinositol, maltotinose and 1-sorbose.

It is to be understood that the foregoing list of compounds believed to be useful as first polyhydroxy compounds in the invention is not intended to be exhaustive, since the usefulness of other polyhydroxy compounds can be readily empirically determined by those skilled in the art.

Glucose must not be used as a polyhydroxy compound in the practice of this invention, since contact of hemoglobin with glucose will result in an apparent increase in the concentration of glycosylated hemoglobin in the sample.

If desired, mixtures of two or more polyhydroxy compounds may be utilized in the lipid and stroma removal step.

Although not required, a polyhydroxy compound may also be present during the lysing step described above in order to maximize protection against oxidation. It will be recognized by those skilled in the art, however, that addition of such a compound may not be practical when red blood cells are lysed by mechanical means, such as freeze/thaw cycles.

After separation of the hemoglobin-rich fraction from the remainder of the mixture, the hemoglobin-rich fraction is dialyzed against an aqueous solution of a second polyhydroxy compound in order to remove residual detergent and organic solvent from the hemoglobin solution. Preferably, the dialysis solution will comprise a 10% (w/v) aqueous sucrose solution, and fresh dialysis solution will be provided to the dialysis system as needed.

The function of the dialysis step is to prevent autooxidation by substitution of a polyhydroxy compound for residual detergent and organic solvent in the hemolysate. It is believed that the polyhydroxy compound present in the dialysate interferes with the steric properties of the hemoglobin to prevent oxidation.

The second polyhydroxy compound may, but need not necessarily, be the same compound, as the first polyhydroxy compound used in the stroma removal step described above. A mixture of suitable polyhydroxy compounds may be utilized in the dialysis step, if desired. However, if the dialysate is to be subjected to lyophilization, as described below, the second polyhydroxy compound must be one which is capable of freezing, such as sucrose or sorbital, for example.

If the first polyhydroxy compound is one which is not capable of freezing, dialysis performs the additional function of substituting a freezable second polyhydroxy compound for the first compound in the dialysate.

After dialysis is complete, the resulting dialysate's optical density is preferably adjusted to approximate that of a whole blood sample which is to be analyzed. This is accomplished by dilution of the dialysate with distilled water, and addition of an aqueous solution of sucrose or another second polyhydroxy compound. Typically, the resulting optical density of the dialysate solution should be about 0.360 at 415 nm.

Although the dialysate solution may be used directly as a standard or control material, it is preferred that the dialysate be lyophilized to provide a dry product suitable for reconstitution. It has been found that the dry hemoglobin product consists essentially of oxyhemoglobin, and sucrose (or other second polyhydroxy compound). The control material may contain trace amounts of methemoglobin, the concentration of which tends to increase with time if stored at ambient temperatures. Therefore, it is desirable to store the lyophilized product at a low temperature, such as 4° C., in order to minimize the conversion of oxyhemoglobin to methemoglobin.

It is further desirable to store the material under non-oxidizing conditions, such as in a nitrogen or inert gas atmosphere.

The resulting dry product is suitable for reconstitution with distilled water or with any of a number of commercially available buffer solutions used in column chromatography or other hemoglobin Alc assay techniques.

The reconstituted hemoglobin solution is usable as both a control material and a standard for various glycosylated hemoglobin determination methods, including electrophoretic and microcolumn or other chromatographic assays. Further, these materials can be used as controls for the measurement of total hemoglobin.

Upon reconstitution, the control material is nonturbid and is substantially free of particulate matter and lipids. The control material, either in dry form or solution form, has a longer shelf life than prior hemoglobin control materials. This is believed to be due to the elimination or minimization of autooxidation by the use of a polyhydroxy compound with an organic solvent in the stroma separation step, and in the dialysis step. Also, the organic solvent sterilizes the hemoglobin during stroma removal. As a result, preservatives are not required.

The practice of the present invention is illustrated by means of the following specific examples. It is to be understood, however, that the examples are intended to be illustrative only, and no unnecessary limitations are to be inferred therefrom, as modifications within the scope of the invention will be apparent to those skilled in the art.

EXAMPLES

Example 1

Preparation of Lyophilized Hemoglobin Control Material from a Blood Sample Obtained from a Normal Patient A sample of whole blood from a normal patient was collected in an EDTA-containing tube, and 17 ml of the sample was introduced to a 50 ml plastic tube. 17 ml of an aqueous NaCl solution (0.85% (w/v) NaCl) was added to the plastic tube, and the contents of the tube were mixed gently for 30 seconds. The mixture was then centrifuged at 4° C. and 8000 rpm (Sorvall Super Speed Automatic Centrifuge, Model SS-3) for 20 minutes. The supernatant liquid was then carefully removed from the red blood cell pellet by pipetting.

8.5 ml of the 0.85% (w/v) NaCl solution was then added to the red blood cells remaining in the plastic tube, and gently mixed therewith for 30 seconds. The mixture was then centrifuged at 4° C. and 8000 rpm (Sorvall SS-3) for 20 minutes. The supernatant was then carefully removed, and the washing and centrifuging step was repeated.

The washed red blood cells were transferred to a 50 ml glass measuring cylinder. The plastic tube which contained the red blood cells was rinsed with a small quantity of 3.0% (w/v) aqueous Triton ® X-100 (a trademark of Rohm and Haas Co.) solution and the contents were transferred to the glass measuring cylinder. The total volume in the cylinder was adjusted to 17 ml with 0.3% (w/v) aqueous Triton ® X-100 solution, and 1.7 g sucrose (Mallinckrodt, Inc. Product No. 8360) was added. The contents of the tube were then stirred at room temperature for 10 minutes and lysing of the red blood cells was observed.

7.65 ml of toluene (Baker Chemical Co., Product No. 1-9456) was then added to the hemolysate solution, and the solution stirred at room temperature for 15 minutes. The toluene-sucrose-hemolysate solution was then transferred to a 50 ml glass tube having a plastic cap, and centrifuged (Beckman Model TJ-6) at 2900 rpm and room temperature for 15 minutes. After centrifugation, the formation of two distinct layers in the glass tube was observed.

The bottom hemoglobin-containing layer, which was crystal clear, was carefully pipetted from the tube and then dialyzed against 4 liters of 10% (w/v) aqueous sucrose solution 24 hours at 4° C. in order to substitute sucrose for residual toluene and Triton ® X-100 in the hemoglobin solution. Fresh sucrose solution was supplied three times during dialysis.

100 μl of the dialysate was diluted to 400 μl by addition of distilled water, 20 μl of the dilute solution was added to 10 ml distilled water, and the optical density at 415 nm was determined (Beckman Model 25 spectrophotometer). The dialysate was then diluted with 10% (w/v) aqueous sucrose solution and the optical density monitored until the dialysate's optical density at 415 nm was 0.360, which approximates the optical density of whole blood at the dilution at which blood is analyzed by a commercially available microcolumn chromatography system, described below.

250 μl aliquots of the dilute analysis were then transferred to 5 ml amber glass vials having siliconized gray rubber stoppers. The contents of the vials were lyophilized in a Hull Corporation (Hatboro, Pa.) Model 651 M 24 F 40 Lyophilizer.

Samples of the lyophilized material were stored at −20° C. and at 4° C. for various periods of time as described below. The lyophilized control material will be referred to herein as a "Hemoglobin Normal Control".

Example 2

Preparation of Lyophilized Hemoglobin Control Material from a Blood Sample Obtained from a Diabetic Patient The procedure of Example 1 was repeated, using a blood sample obtained from a diabetic patient. The resulting lyophilized control material will be referred to herein as a "Hemoglobin Medium-High Control".

Example 3

Reconstitution of Lyophilized Control Materials

For use as a standard or control material in glycosylated hemoglobin electrophoresis or microcolumn chromatography, the lyophilized materials of Examples 1 and 2 can be reconstituted with 1 ml of either distilled water, a hemolysis reagent or an elution buffer used in commercial microcolumn chromatography methods described below. Preferably, the lyophilized control materials are reconstituted with distilled water or elution buffer, since the hemoglobin value of a control material reconstituted with a hemolysis reagent tends to increase after storage for two weeks at 4° C.

For use as a control material for total hemoglobin determination, the lyophilized materials of Examples 1 and 2 can be reconstituted with distilled water to obtain desired hemoglobin concentrations, as detailed in Example 13.

Examples 4–11

Nature of the Control Materials

Examples 4–11, in conjunction with FIGS. 1–8, demonstrate the hemoglobin composition of freshly-drawn whole blood samples from normal and diabetic patients and the respective glycosylated hemoglobin fractions thereof in comparison with the hemoglobin composition of reconstituted lyophilized control materials made according to Examples 1–3 and their respective glycosylated hemoglobin fractions. Examples 4–11 in FIGS. 1–8 were obtained by means of absorption spectroscopy using a Beckman Model 25 spectrophotometer. Separations of glycosylated hemoglobin fractions from the reconstituted control materials and from freshly-drawn human blood samples were carried out on the Isolab, Inc. (Akron, Ohio) Quik-Sep® Fast Hemoglobin™ Test System.

Example 4

Figure 1:
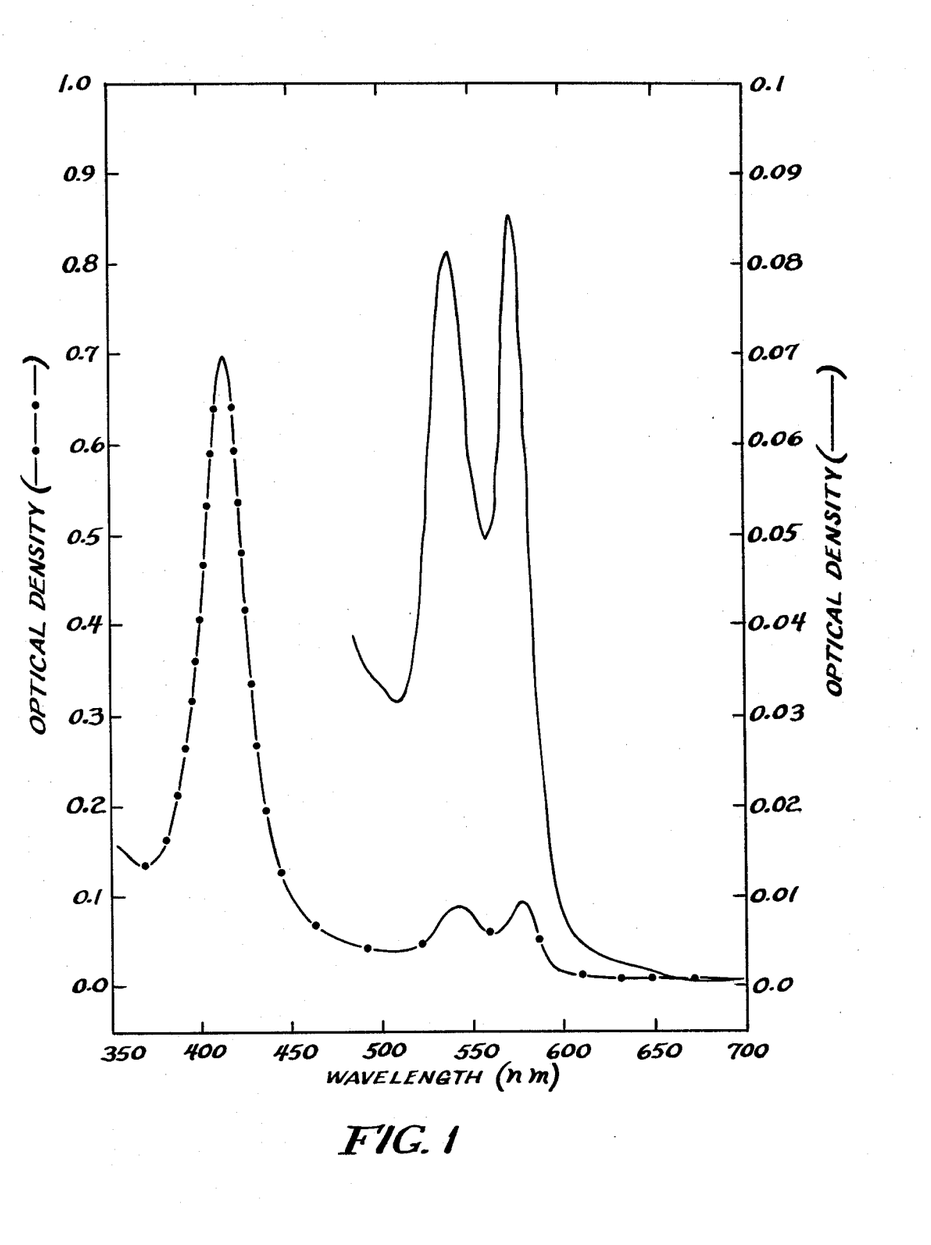
FIG. 1 is an absorption spectrum of a freshly-drawn blood specimen obtained from a normal human subject.
Figure 2:
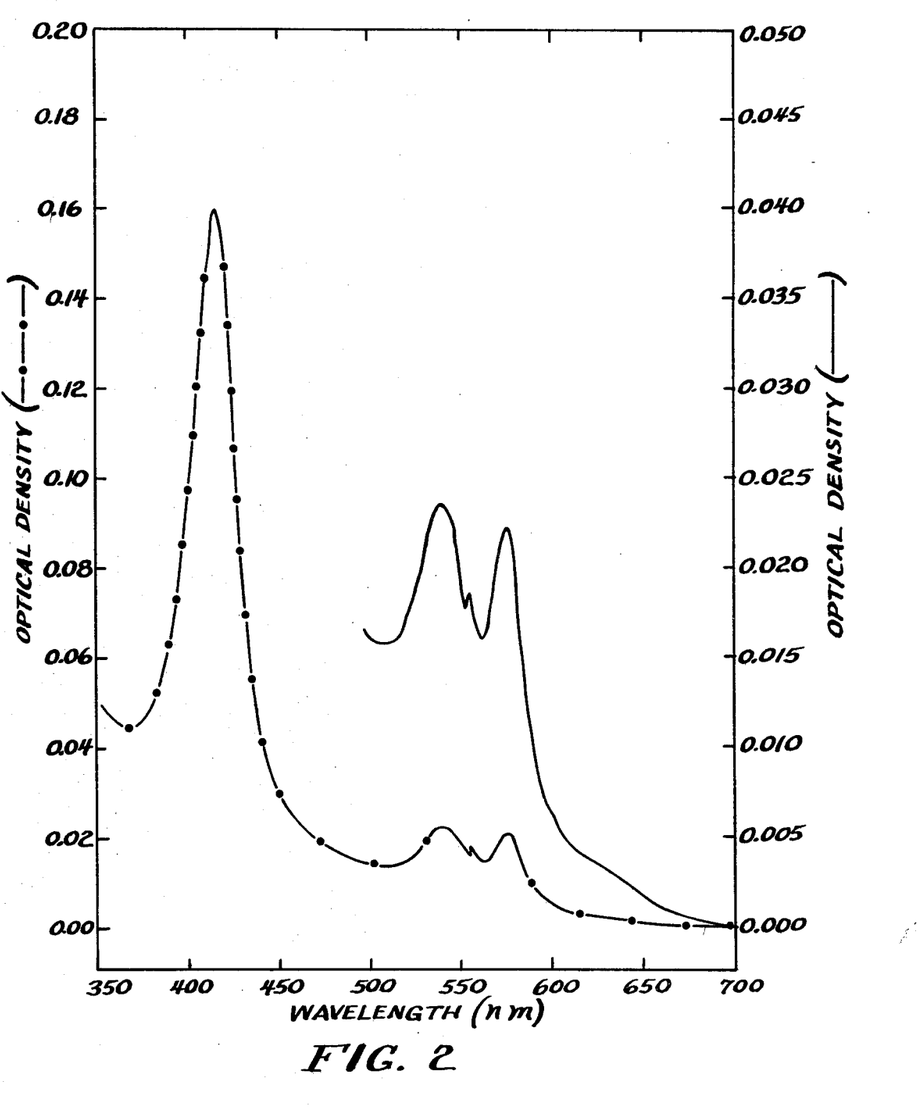
FIG. 2 is an absorption spectrum of the glycosylated hemoglobin fraction of the blood specimen of FIG. 1.
Figure 3:
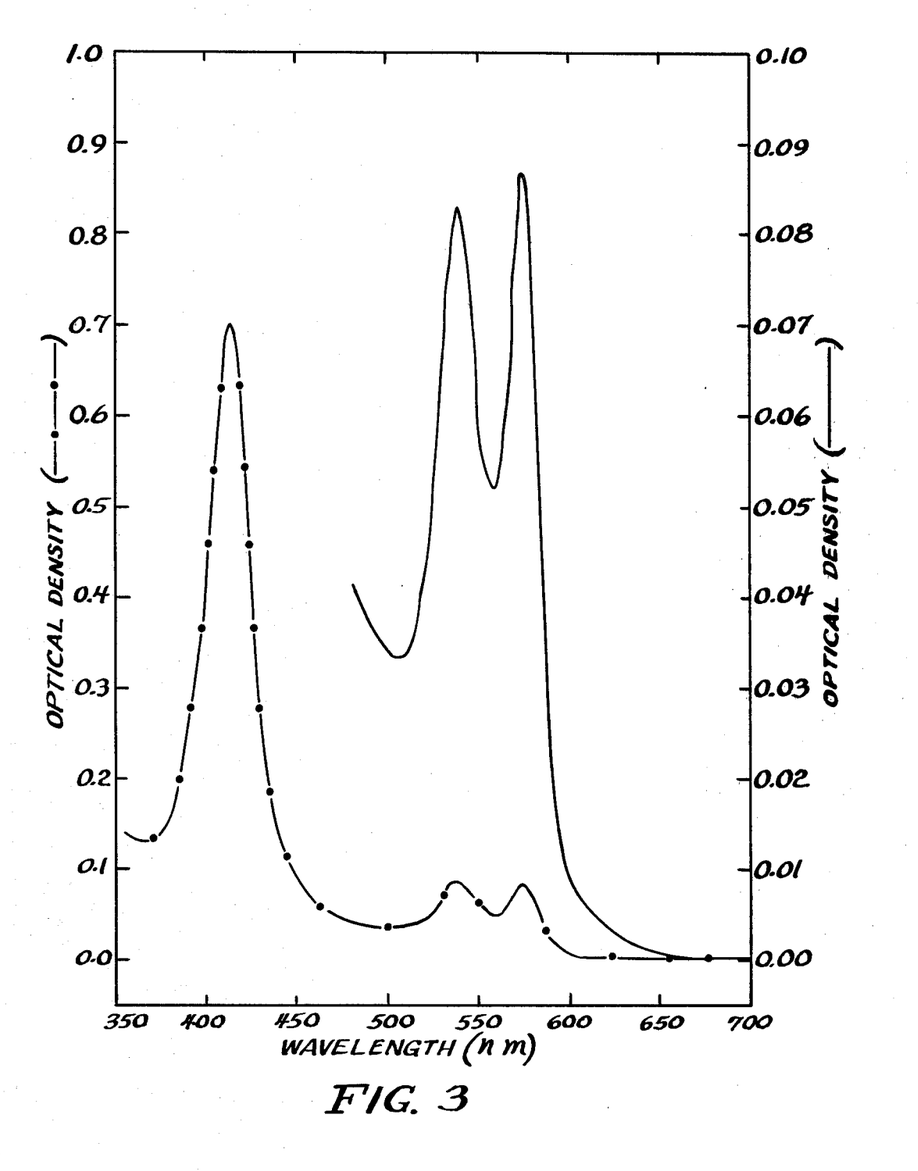
FIG. 3 is an absorption spectrum of a freshly-prepared, lyophilized normal hemoglobin control material made according to the invention from the blood specimen of FIG. 1.
Figure 4:
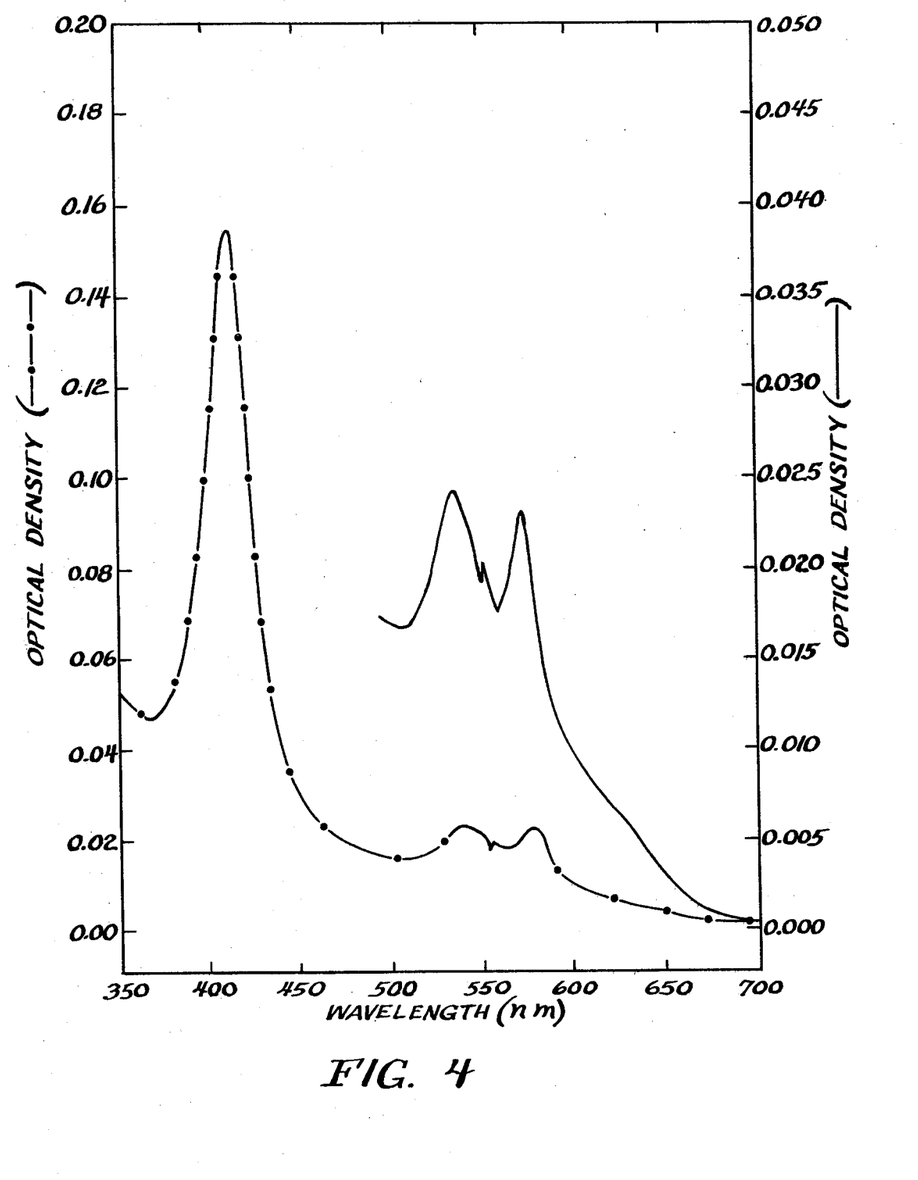
FIG. 4 is an absorption spectrum of the glycosylated hemoglobin fraction of the lyophilized control material of FIG. 3.

Absorption Spectrum of a Freshly-Drawn Blood Specimen Obtained from a Normal Subject 100 μl of whole blood collected from a normal human subject in an EDTA was hemolyzed with 500 μl of Isolab Hemolysis Reagent. 20 μl of the hemolyzed blood specimen was added to 5 ml distilled water and the absorption spectrum was scanned between 350 and 700 nm, and is shown by the broken line in FIG. 1. The expanded absorption spectrum between 500 and 700 nm is shown by the solid line in FIG. 1.

Example 5

Absorption Spectrum of the Glycosylated Hemoglobin Fraction of a Freshly-Drawn Blood Specimen Obtained from a Normal Patient 50 μl of the hemolyzed blood specimen of Example 4 was introduced to the Isolab microcolumn and 4 ml of Isolab Fast Hb Elution Solution was added to the column and the glycosylated hemoglobin fraction was collected. The absorption spectrum of the glycosylated hemoglobin fraction so obtained was scanned between 350 and 700 nm, and the absorption spectrum is shown by the broken line in FIG. 2. The expanded absorption spectrum between 500 and 700 nm is shown by the solid line in FIG. 2.

Example 6

Absorption Spectrum of Freshly Prepared Hemoglobin Normal Control

The lyophilized Hemoglobin Normal Control material of Example 1 was reconstituted with 1 ml of Isolab Hemolysis Reagent. 20 μl of the reconstituted control material was added to 5 ml distilled H₂O and the absorption spectrum of the reconstituted material was scanned between 350 and 700 nm. The spectrum is shown by the broken line in FIG. 3. The expanded absorption spectrum between 500 and 700 nm is shown by the solid line in FIG. 3.

Example 7

Absorption Spectrum of the Glycosylated Hemoglobin Fraction of Freshly-Prepared Lyophilized Hemoglobin Normal Control The lyophilized Hemoglobin Normal Control material of Example 1 was reconstituted with 1 ml of Isolab Hemolysis Reagent. 50 μl of the reconstituted control material was introduced to the Isolab microcolumn and 4 ml of the Isolab Fast Hb Elution Solution was added to the column and the glycosylated hemoglobin fraction was collected. The absorption spectrum of the glycosylated hemoglobin fraction was scanned between 350 and 700 nm and is shown by the broken line in FIG. 4. The expanded absorption spectrum between 500 and 700 nm is shown by the solid line in FIG. 4.

Example 8

Figure 5:
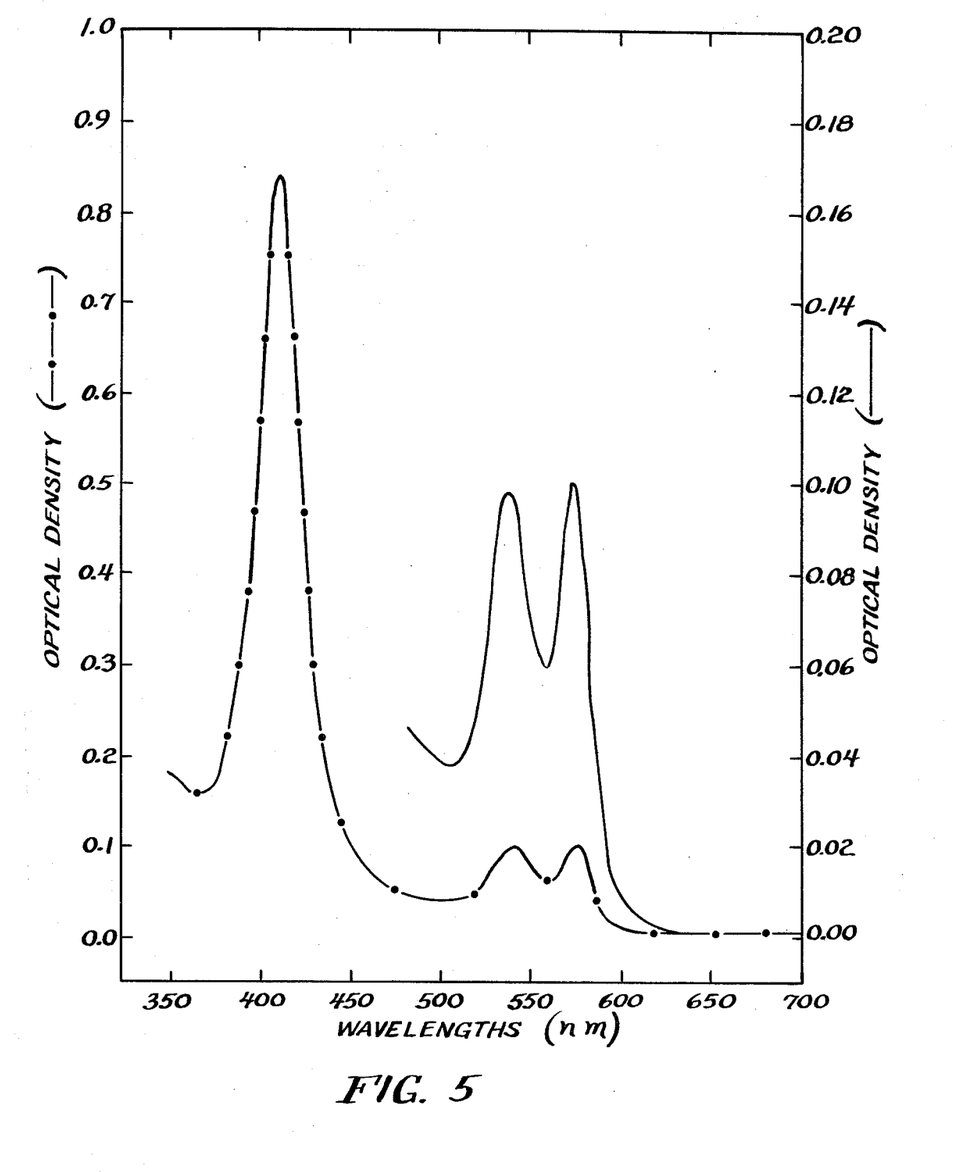
FIG. 5 is an absorption spectrum of a freshly-drawn blood specimen obtained from a diabetic patient.
Figure 6:
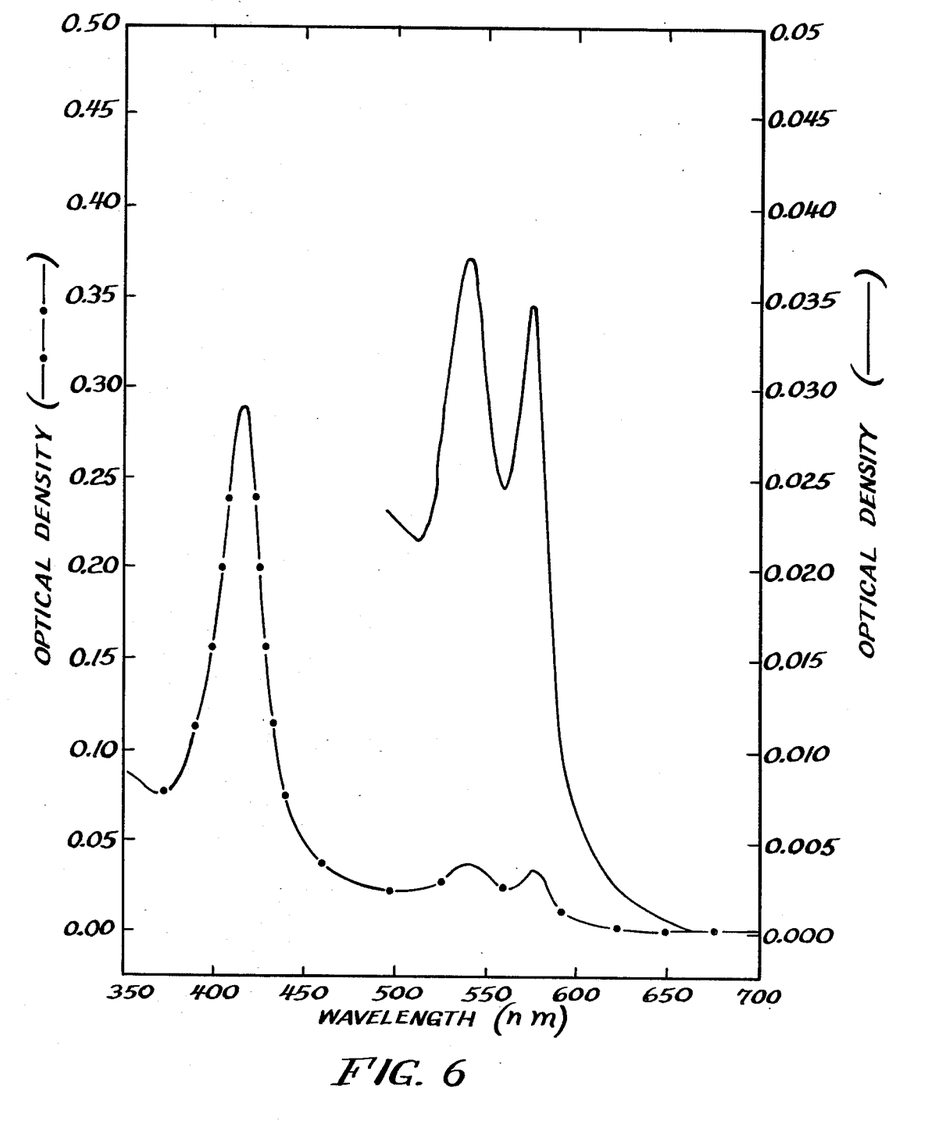
FIG. 6 is an absorption spectrum of the glycosylated hemoglobin fraction of the blood specimen of FIG. 5.

Absorption Spectrum of a Freshly-Drawn Blood Specimen Obtained from a Diabetic Subject 100 μl of whole blood collected in an EDTA tube from a human diabetic patient was hemolyzed with 500 μl of the Isolab Hemolysis Reagent. 20 ml of the hemolyzed blood specimen was added to 5 ml distilled H₂O and the absorption spectrum was scanned between 350 and 700 nm, as shown by the broken line in FIG. 5. The expanded absorption spectrum between 500 and 700 nm is shown by the solid line in FIG. 5.

Example 9

Absorption Spectrum of the Glycosylated Hemoglobin Fraction of a Freshly-Drawn Blood Specimen from a Diabetic Patient 50 μl of the hemolyzed blood specimen of Example 8 was introduced to the Isolab microcolumn and 4 ml of the Isolab Fast Hb Elution Solution was added to the column and the glycosylated hemoglobin fraction was collected. The absorption spectrum of the glycosylated hemoglobin fraction was scanned between 350 and 700 nm as shown by the broken line in FIG. 6. The expanded absorption spectrum between 500 and 700 nm is shown by the solid line in FIG. 6.

Example 10

Figure 7:
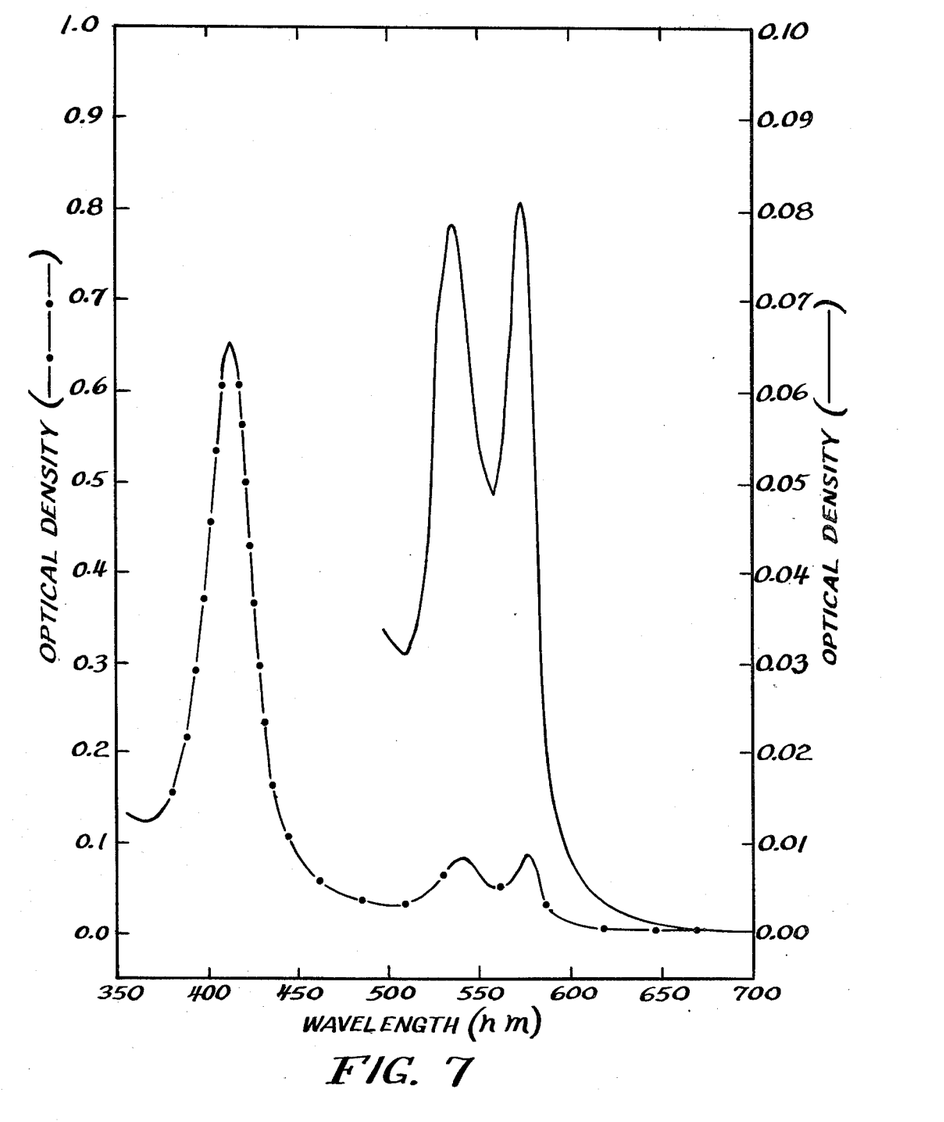
FIG. 7 is an absorption spectrum of a freshly-prepared lyophilized hyperglycemic hemoglobin control material made according to the invention from the blood specimen of FIG. 5.
Figure 8:
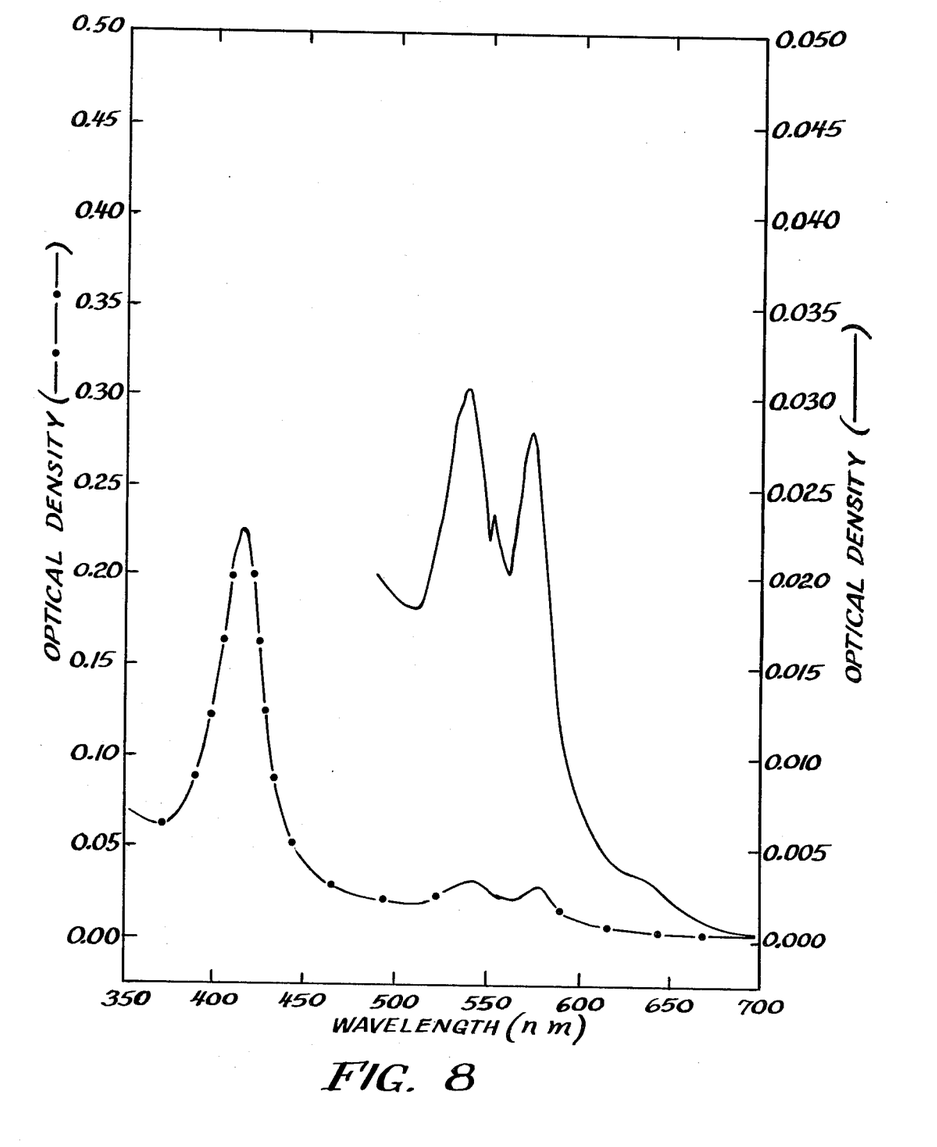
FIG. 8 is an absorption spectrum of the glycosylated hemoglobin fraction of the lyophilized control material of FIG. 7.

Absorption Spectrum of Freshly-Prepared Lyophilized Hemoglobin Medium-High Control The lyophilized Hemoglobin Medium-High Control of Example 2 was reconstituted with 1 ml of Isolab Hemolysis Reagent. 20 μl of the reconstituted control material was added to 5 ml distilled $H_2O$ and the absorption spectrum of the reconstituted material was scanned between 350 and 700 nm as shown by the broken line in FIG. 7. The expanded absorption spectrum between 500 and 700 nm is shown by the solid line in FIG. 7.

Example 11

Absorption Spectrum of the Glycosylated Hemoglobin Fraction of Freshly-Prepared Lyophilized Hemoglobin Medium-High Control The lyophilized Hemoglobin Medium-High Control material of Example 2 was reconstituted with 1 ml of Isolab Hemolysis Reagent. 50 μl of the reconstituted control material was introduced to the Isolab microcolumn and 4 ml of Isolab Fast Hb Elution Solution was added to the column and the glycosylated hemoglobin fraction was collected. The absorption spectrum of the glycosylated hemoglobin fraction was scanned between 350 and 700 nm as shown by the broken line in FIG. 8. The expanded absorption spectrum between 500 and 700 nm is shown by the solid line in FIG. 8.

The foregoing examples, taken in conjunction with FIGS. 1–8, demonstrate that the absorption spectra of the reconstituted lyophilized Hemoglobin Control materials, and their respective glycosylated hemoglobin fractions obtained by microcolumn chromatography, are substantially identical to absorption spectra obtained from freshly-drawn blood samples and their respective glycosylated hemoglobin fractions. This is true for both normal and diabetic patients.

Therefore, it will be appreciated that the method of preparing hemoglobin control materials of the invention provides a reliable, accurate standard or control material for use in column chromatography or electrophoretic determination of glycosylated hemoglobin and total hemoglobin.

Examples 12–13

Stability of Lyophilized and Reconstituted Hemoglobin Control Materials

Example 12

Stability of Lyophilized and Reconstituted Hemoglobin Control Materials as Determined by Microcolumn Chromatography Specimens of the lyophilized hemoglobin control materials of Examples 1 and 2 were stored under different temperature conditions for various periods of time. The aged lyophilized control materials were then reconstituted with 1 ml of Isolab Hemolysis Reagent, and assayed for the percentage of glycosylated hemoglobin by microcolumn chromatography using the Isolab, Inc. Quik-Sep ® Fast Hemoglobin ™ system using the following procedure: 50 μl of the reconstituted control material was introduced to the Isolab microcolumn and 4 ml of Isolab Fast Hb Elution Solution was added to the column and, the glycosylated hemoglobin fraction was collected. The optical density of the glycosylated hemoglobin fraction was read at 415 nm with a Gilford Spectrophotometer. Total hemoglobin was determined by diluting 20 μl of the reconstituted hemolysate with 10 ml distilled $H_2O$ and the optical density was read at 415 nm.

The results of these tests are shaon in Table 1 and indicate that the lyophilized control materials of Examples 1 and 2 are stable at 37° C. for at least 4 days, at room temperature for at least 40 days, at 4° C. for at least 4 months and at −20° C. for at least 4.5 months.

Samples of the reconstituted control materials were stored at 4° C. for up to 8 days, and assayed for the percentage of glycosylated hemoglobin using a microcolumn chromatography procedure essentially equivalent to the Isolab, Inc. procedure described above. The results of these tests are shown in Table 2 and indicate that the reconstituted control materials of Examples 1 and 2 are stable at 4° C. for at least 8 days.

The coefficients of variation shown in Tables 1 and 2 are believed to be due to column variables rather than to variables inherent in the control materials.

TABLE 1

STABILITY OF THE LYOPHILIZED HEMOGLOBIN CONTROL MATERIALS OF EXAMPLES 1 AND 2
Percentage of Glycosylated Hemoglobin of the Lyophilized
Hemoglobin Control Materials as Determined by Isolab, Inc. Microcolumn Chromatography

| Storage Condition | Normal Control (Example 1) | Medium-High Control (Example 2) |
|---|---|---|
| 1. Freshly Drawn Blood | 7.32% | 11.60% |
| 2. Room Temperature, 4 weeks | 6.74 | 10.83 |
| Room Temperature, 40 days | 6.80 | — |
| 3. 37° C., 2 days | 7.22 | 11.28 |
| 37° C., 4 days | 7.45 | 11.63 |
| −20° C. (Control Experiment) | 7.55 | 11.43 |
| 4. 4° C., 3 months | 6.98 | 11.17 |
| 4° C., 4 months | 7.18 | 11.29 |
| 5. −20° C., 3.5 months | 7.35 | 10.92 |
| −20° C., 4.5 months | 7.08 | 11.22 |

TABLE 1-continued

STABILITY OF THE LYOPHILIZED HEMOGLOBIN CONTROL
MATERIALS OF EXAMPLES 1 AND 2
Percentage of Glycosylated Hemoglobin of the Lyophilized
Hemoglobin Control Materials as Determined by Isolab, Inc. Microcolumn Chromatography

| Storage Condition | Normal Control (Example 1) | Medium-High Control (Example 2) |
|---|---|---|
| | Mean = 7.17% | Mean = 11.26% |
| | Standard Deviation = 0.268 | Standard Deviation = 0.272 |
| | Coefficient of Variation = 3.74% | Coefficient of Variation = 2.42% |

TABLE 2

STABILITY OF THE RECONSTITUTED HEMOGLOBIN CONTROLS
Percentage of the Glycosylated Hemoglobin of the Reconstituted Hemoglobin
Control Materials as Determined by Microcolumn Chromatography

| Days After Reconstitution (The Reconstituted Hemolysates Were Stored at 4° C.) | Normal Control (Example 1) | Medium-High Control (Example 2) |
|---|---|---|
| Day 0 | 6.97% | 11.1% |
| Day 1 | 7.12 | 11.0 |
| Day 2 | 6.78 | 11.4 |
| Day 3 | 6.97 | 11.0 |
| Day 4 | 7.46 | 11.9 |
| Day 6 | 7.31 | 11.3 |
| Day 7 | 7.13 | 11.0 |
| Day 8 | 7.30 | 11.2 |
| | Mean = 7.13% | Mean = 11.22% |
| | Standard Deviation = 0.222 | Standard Deviation = 0.307 |
| | Coefficient of Variation = 3.11% | Coefficient of Variation = 2.73% |

Example 13

Stability of the Lyophilized and Reconstituted Hemoglobin Control Materials of Examples 1 and 2 as Determined by Total Hemoglobin Determination The lyophilized glycosylated hemoglobin control materials of Examples 1 and 2 were stored under different conditions as shown in Table 3. Samples of the aged lyophilized hemoglobin control materials were then reconstituted with 1 ml of Isolab Hemolysis Reagent or with 1 ml of distilled H₂O, and stored at 4° C. for various periods of time, as shown in Table 2. The total hemoglobin of each sample was assayed with the Drabkin's based cyanomethemoglobin assay system sold by Lancer Division, Sherwood Medical Industries Inc. (Foster City, Calif.) under the trademark "Lancer Hemoglobin Analyzer". The results of these tests as shown in Table 3 indicate that the lyophilized hemoglobin control materials of Examples 1 and 2 are suitable for use as controls in total hemoglobin determination. Further, the lyophilized control materials can be reconstituted with 0.2 ml, 0.4 ml and 0.8 ml of distilled H₂O to obtain hemoglobin concentrations of about 10, 5 and 2.5 g/dl, respectively.

TABLE 3

STABILITY OF THE LYOPHILIZED HEMOGLOBIN CONTROL
MATERIALS OF EXAMPLES 1 AND 2
Total Hemoglobin Determination by the Lancer Hemoglobin Analyzer

| Storage Condition | Hemoglobin Concentration | |
|---|---|---|
| | Normal Control (Example 1) | Medium-High Control (Example 2) |
| 1. Freshly prepared lyophilized controls | 2.1 g/dl | 2.0 g/dl |
| 2. Lyophilized controls stored at −20° C. and then reconstituted and stored at 4° C. for 8 days. | 2.1 | 2.1 |
| 3. Lyophilized controls stored at 37° C. for 3 days and then reconstituted and stored at 4° C. for 8 days. | 2.1 | 2.0 |
| 4. Lyophilized controls stored at 37° C. for 7 days and then reconstituted and stored at 4° C. for 3 days. | 2.1 | 2.0 |
| 5. Lyophilized controls stored at room temperature for 7 days and then reconstituted and stored at 4° C. for 11 days. | 2.1 | 2.1 |
| 6. Lyophilized controls stored at room temperature for 14 days and then reconstituted and stored at 4° C. for 3 days. | 2.1 | 2.0 |
| 7. Lyophilized controls stored at room temperature for 28 days and then reconstituted. | 2.1 | 2.0 |
| 8. Lyophilized controls stored at 4° C. for 14 days and then reconstituted. | 2.1 | 2.0 |
| 9. Lyophilized controls stored at 4° C. for 3 months and then reconstituted. | 2.2 | 2.2 |
| 10. Lyophilized controls stored at 4° C. for 4 months and then reconstituted. | 2.2 | 2.1 |
| 11. Lyophilized controls stored at −20° C. for 3 months and then reconstituted. | 2.2 | 2.2 |
| 12. Lyophilized controls stored at −20° C. for 5 months and | 2.1 | 2.0 |

TABLE 3-continued

STABILITY OF THE LYOPHILIZED HEMOGLOBIN CONTROL
MATERIALS OF EXAMPLES 1 AND 2
Total Hemoglobin Determination by the Lancer Hemoglobin Analyzer

| | Hemoglobin Concentration | |
|---|---|---|
| Storage Condition | Normal Control (Example 1) | Medium-High Control (Example 2) |
| then reconstituted. | Mean = 2.12 g/dl | Mean = 2.06 g/dl |

Examples 14–15

Characterization of Lyophilized Hemoglobin Control Materials

Example 14

Absorption Spectrophotometry of Lyophilized Hemoglobin Control Materials of Examples 1 and 2

Tables 4 and 5 list various spectral properties of hemoproteins and heme derivatives. Specimens of the lyophilized hemoglobin control materials of Examples 1 and 2 were stored at 37° C. for 4 days, at room temperature for 40 days, at 4° C. for 4 months and at −20° C. for 4.5 months. The aged lyophilized hemoglobin control materials were then reconstituted with 1 ml of Isolab Hemolysis Reagent. 20 μl of each reconstituted specimen was diluted with 5 ml of distilled $H_2O$ and the absorption spectrum of each specimen was scanned from 350 to 700 nm.

Table 6 shows the absorbance of the reconstituted Hemoglobin Normal Control materials of Example 1 at λ max for hemiglobin, and oxyhemoglobin ($\alpha$, $\beta$ and Soret).

In Table 6, no significant peak at 630 nm (λ max for methemoglobin) was observed. The absorbances at 577 nm, 541 nm and 415 nm (Soret) indicate that the hemoglobin of the control material of Example 1 consisted essentially of oxyhemoglobin.

Table 7 shows the absorbance of the reconstituted Hemoglobin Medium-High Control material of Example 2 at λ max for hemiglobin and oxyhemoglobin ($\alpha$, $\beta$ and Soret).

In Table 7, a small peak at 630 nm was noted for the control which was stored at 37° C. for 4 days. This indicates that a small amount of methemoglobin had formed. However, this does not affect the performance of the microcolumn chromatography.

TABLES 4 AND 5

PROPERTIES OF HEMOPROTEINS AND HEMIPROTEINS

TABLE 4

| Compound | Ligands Fifth | Ligands Sixth | μ (BM)[a] | Unpaired Electrons | Designation | λ Max. $\alpha$ | λ Max. $\beta$ | λ Max. Soret | E'O, in Volts |
|---|---|---|---|---|---|---|---|---|---|
| Hemoglobin (myoglobin) | His[b] | $H_2O$ | 4.47 | 4 | High-spin octahedral | 555 | — | 430 | −0.130 0.00 (myoglobin) |
| Oxyhemoglobin | His | $O_2$ | 0 | 0 | Low-spin octahedral | 577 | 541 | 414 | |
| Carboxyhemoglobin | His | CO | 0 | 0 | Low-spin octahedral | 570 | 538 | 418 | |
| Cyanhemoglobin | | CN— | 0 | 0 | Low-spin octahedral | | | | |
| Nitric oxide Hb | | NO | | 1 | | | | | |

[a]Bohr magnetons
[b]Histidine

TABLE 5

| Compound | Ligands Fifth | Ligands Sixth | μ (BM)[c] | Unpaired Electrons | Designation[d,e] | λ Max. $\alpha$ | λ Max. $\beta$ | λ Max. Soret |
|---|---|---|---|---|---|---|---|---|
| Hemiglobin (methemoglobin, metmyoglobin) | His[f] | $OH_2$ | 5.7 | 5 | High-spin octahedral | 630 | 500 | 406 |
| | His | OH— | 4.6 | 1,5 | Mixture of spin states | 500 | (577, 540) | 411 |
| | His | F— | 5.9 | 5 | High spin | 608 | | |
| | His | $HCO_2$— | 5.4 | 5 | High spin | | | |
| | His | CN— | 2.5 | 1 | Low-spin octahedral | | 540 | 415 |
| | His | SH | 2.3 | 1 | Low-spin octahedral | | | |
| | His | $N_3$— | 2.8 | 1 | Low-spin octahedral | 630 | 575 | 420 |
| | His | $NH_3$ | 2.9 | 1 | Low-spin octahedral | | | |
| | His | His[d] | 2.9 | 1 | | | | |

[c]Bohr magneton:
$\sqrt{n(n+2)}$, where n = number of unpaired electrons.
[d]Spin = n/2.
[e]"Low spin" is equivalent to "essentially covalent;" "high spin" to "essentially ionic" bond type (Pauling).
[f]Histidine imidazole N on the protein (globin).

TABLE 6

ABSORPTION SPECTRA OF THE LYOPHILIZED HEMOGLOBIN NORMAL
CONTROL MATERIAL OF EXAMPLE 1 PRIOR
TO MICROCOLUMN CHROMATOGRAPHY

| | Optical Density at λ Max | | | |
|---|---|---|---|---|
| Storage Condition | 630 nm | 577 nm | 541 nm | 415 nm (Soret) |
| 1. Freshly prepared lyophilized | — | 0.087 | 0.084 | 0.701 |

TABLE 6-continued

ABSORPTION SPECTRA OF THE LYOPHILIZED HEMOGLOBIN NORMAL
CONTROL MATERIAL OF EXAMPLE 1 PRIOR
TO MICROCOLUMN CHROMATOGRAPHY

| Storage Condition | Optical Density at λ Max | | | |
|---|---|---|---|---|
| | 630 nm | 577 nm | 541 nm | 415 nm (Soret) |
| normal material | | | | |
| 2. 37° C. for 4 days | — | 0.081 | 0.079 | 0.692 |
| 3. Room temperature for 40 days | — | 0.0782 | 0.0765 | 0.670 |
| 4. 4° C. for 4 months | — | 0.0802 | 0.0790 | 0.688 |
| 5. −20° C. for 4.5 months | — | 0.0833 | 0.0813 | 0.706 |

TABLE 7

ABSORPTION SPECTRA OF THE LYOPHILIZED HEMOGLOBIN
MEDIUM-HIGH CONTROL OF EXAMPLE 2 PRIOR TO
MICROCOLUMN CHROMATOGRAPHY

| Storage Condition | Optical Density at λ Max | | | |
|---|---|---|---|---|
| | 630 nm | 577 nm | 541 nm | 415 nm (Soret) |
| 1. Freshly prepared lyophilized medium-high control | — | 0.081 | 0.0782 | 0.657 |
| 2. 37° C. for 4 days | 0.0085 | 0.0715 | 0.070 | 0.620 |
| 3. Room temperature for 40 days | | | | |
| 4. 4° C. for 4 months | — | 0.0745 | 0.0731 | 0.634 |
| 5. −20° C. for 4.5 months | — | 0.0759 | 0.0749 | 0.649 |

Example 15

Absorption Spectrophotometry of the Glycosylated
Hemoglobin Fraction of Lyophilized Hemoglobin
Control Materials Specimens of the reconstituted Hemoglobin Control materials of Examples 1 and 2 were subjected to the Isolab, Inc. Quick-Sep[R] microcolumn chromatography procedure, after storage under different temperature conditions for various periods of time as follows:

The lyophilized control materials were each reconstituted with 1 ml of Isolab Hemolysis Reagent. 50 μl of each reconstituted specimen was applied to an Isolab microcolumn, and the glycosylated hemoglobin fraction of each specimen was eluted from the column with 4 ml of Isolab Fast Hb Elution Solution, and collected.

The glycosylated hemoglobin fraction of each specimen was scanned for absorption spectra between 350 and 700 nm. Table 8 lists the absorbances at λ max for hemiglobin and oxyhemoglobin (α, β and Soret).

Table 8 shows that trace amounts of methemoglobin (peak at 630 nm) had formed during the storage of the lyophilized hemoglobin control materials at 37° C. for 4 days and at room temperature for 40 days. However, this does not affect the performance of the microcolumn chromatography.

Table 9 shows the absorbances of the reconstituted medium-high control material of Example 2 at λ max for hemiglobin and oxyhemoglobin (α, β and Soret). Similarly to Table 8, small amounts of methemoglobin were detected.

The results of the absorption spectrophotometric tests of Examples 13 and 14 indicate that the lyophilized hemoglobin control materials of Examples 1 and 2 are essentially oxyhemoglobins. Storage at 37° C. and at room temperature tends to increase the trace amounts of methemoglobin present in the control materials. Therefore, these control materials should be stored at low temperatures, such as between about −20° C. and 4° C.

TABLE 8

ABSORPTION SPECTRA OF THE GLYCOSYLATED HEMOGLOBIN FRACTIONS OF THE
LYOPHILIZED HEMOGLOBIN NORMAL CONTROL MATERIALS OF
EXAMPLE 1 AFTER MICROCOLUMN CHROMATOGRAPHY

| Storage Condition | Optical Density at λ Max | | | | |
|---|---|---|---|---|---|
| | 630 nm | 577 nm | 556 nm[a] | 541 nm | 415 nm (Soret) |
| 1. Freshly prepared lyophilized normal material | — | 0.023 | 0.020 | 0.024 | 0.154 |
| 2. 37° C. for 4 days | 0.003 | 0.0186 | 0.017 | 0.0215 | 0.152 |
| 3. Room temperature for 40 days | 0.003 | 0.0185 | 0.017 | 0.0205 | 0.141 |
| 4. 4° C. for 4 months | — | 0.0186 | 0.0168 | 0.022 | 0.153 |
| 5. −20° C. for 4.5 months | — | 0.019 | 0.017 | 0.0225 | 0.154 |

[a]A small peak at 556 nm was observed in the glycosylated hemoglobin fractions; whereas, the whole hemoglobin solution did not show a distinguished peak at 556 nm.

TABLE 9

ABSORPTION SPECTRA OF THE GLYCOSYLATED HEMOGLOBIN FRACTIONS
OF THE LYOPHILIZED HEMOGLOBIN
MEDIUM-HIGH CONTROL MATERIAL
OF EXAMPLE 2 AFTER MICROCOLUMN CHROMATOGRAPHY

| Storage Conditions | Optical Density at λ Max | | | | |
|---|---|---|---|---|---|
| | 630 nm | 577 nm | 556 nm[a] | 541 nm | 415 nm (Soret) |
| 1. Freshly prepared lyophilized | — | 0.028 | 0.0235 | 0.030 | 0.225 |

TABLE 9-continued
ABSORPTION SPECTRA OF THE GLYCOSYLATED HEMOGLOBIN FRACTIONS
OF THE LYOPHILIZED HEMOGLOBIN
MEDIUM-HIGH CONTROL MATERIAL
OF EXAMPLE 2 AFTER MICROCOLUMN CHROMATOGRAPHY

| Storage Conditions | Optical Density at λ Max | | | | |
|---|---|---|---|---|---|
| | 630 nm | 577 nm | 556 nm[a] | 541 nm | 415 nm (Soret) |
| medium-high control | | | | | |
| 2. 37° C. for 4 days | 0.005 | 0.0286 | 0.0235 | 0.0310 | 0.225 |
| 3. Room temperature for 40 days | | | | | |
| 4. 4° C. for 4 months | — | 0.0267 | 0.0225 | 0.0301 | 0.222 |
| 5. −20° C. for 4.5 months | — | 0.0260 | 0.0220 | 0.0295 | 0.216 |

[a]A small peak at 556 nm was observed in the glycosylated hemoglobin fraction; whereas, the whole hemoglobin solution did not show a distinguished peak at 556 nm.

The foregoing detailed description is given for clearness of understanding only, and no unnecessary limitations are to be understood therefrom, as modifications will be obvious to those skilled in the art.

We claim:

1. A method of preparing a hemoglobin control material, said method comprising the steps of:
   (a) hemolyzing red blood cells to form a reaction mixture;
   (b) removing lipids and stroma from said reaction mixture by mixing said reaction mixture with an organic solvent immiscible with said reaction mixture and a first polyhydroxy compound to form a hemoglobin-rich first fraction, and a second fraction;
   (c) separating said first and second fractions; and,
   (d) removing residual organic solvent from said first fraction to obtain a hemoglobin-rich solution.

2. The method of claim 1 wherein said first polyhydroxy compound is selected from the class consisting of sucrose, sorbitol, glycerol, alkylene glycols, mono-saccharides, poly-saccharides and polyhydroxy carbohydrates.

3. The method of claim 2 wherein said first polyhydroxy compound is sucrose.

4. The method of claim 1 wherein said organic solvent is toluene.

5. A method of preparing a hemoglobin control material, said method comprising the steps of:
   (a) hemolyzing red blood cells to form a reaction mixture;
   (b) removing lipids and stroma from said reaction mixture by mixing said reaction mixture with an organic solvent immiscible with said reaction mixture and a first polyhydroxy compound to form a hemoglobin-rich first fraction, and a second fraction;
   (c) separating said first and second fractions; and,
   (d) removing residual organic solvent from said first fraction by dialysis of said first fraction against a solution of a second polyhydroxy compound to obtain a hemoglobin-rich solution.

6. The method of claim 5 wherein said second polyhydroxy compound comprises said first polyhydroxy compound.

7. The method of claim 5 wherein said second polyhydroxy compound differs from said first polyhydroxy compound, and said second polyhydroxy compound is substituted for said first polyhydroxy compound and said residual organic solvent in said first fraction in said dialysis step.

8. A method of preparing a hemoglobin control material, said method comprising the consecutive steps of:
   (a) hemolyzing red blood cells by mixing said red blood cells with a detergent to form a reaction mixture;
   (b) mixing said reaction mixture with toluene and sucrose to form a hemoglobin-rich first fraction and a second fraction immiscible with said first fraction;
   (c) separating said first and second fractions;
   (d) dialyzing said first fraction against an aqueous sucrose solution to obtain a hemoglobin-rich dialysate comprising hemoglobin, water and sucrose; and,
   (e) lyophilizing said dialysate to provide a dry hemoglobin control material which is suitable for reconstitution.

9. The method of claim 8 wherein said hemolysis ste is carried out in the presence of sucrose.

10. The method of claim 8 including the additional step of adjusting the optical density of said dialysate prior to lyophilization by addition of an aqueous sucrose solution thereto such that the optical density of said diluted dialysate approximates that of whole blood.

11. A method of preparing a hemoglobin control material, said method comprising the steps of:
   (a) hemolyzing red blood cells in the presence of a first polyhydroxy compound to form a reaction mixture;
   (b) removing lipids and stroma from said reaction mixture by mixing said reaction mixture with an organic solvent immiscible with said reaction mixture in the presence of said first polyhydroxy compound to form a hemoglobin-rich first fraction, and a second fraction;
   (c) separating said first and second fractions; and,
   (d) removing residual organic solvent from said first fraction to obtain a hemoglobin-rich solution.

12. The method of claim 11 wherein said first polyhydroxy compound is selected from the class consisting of sucrose, sorbitol, glycerol, alkylene glycols, mono-saccharides, poly-saccharides and polyhydroxy carbohydrates.

13. The method of claim 12 wherein said first polyhydroxy compound is sucrose.

14. A method of preparing a hemoglobin control material, said method comprising the consecutive steps of:
   (a) hemolyzing red blood cells by mixing said red blood cells with a detergent and a first polyhydroxy compound to form a reaction mixture;
   (b) mixing said reaction mixture with an organic solvent immiscible with said reaction mixture, and said first polyhydroxy compound to form a hemoglobin-rich first fraction and a second fraction immiscible with said first fraction;

(c) separating said first and second fractions;

(d) dialyzing said first fraction against an aqueous solution of a second polyhydroxy compound to obtain a hemoglobin-rich dialysate consisting essentially of hemoglobin, water and said second polyhydroxy compound; and, (e) lyophilizing said dialysate to provide a dry hemoglobin control material which is suitable for reconstitution.

15. The method of claim 14 wherein said first polyhydroxy compound is selected from the class consisting of sucrose, sorbitol, glycerol, alkylene glycols, mono-saccharides, poly-saccharides and polyhydroxy carbohydrates.

16. The method of claim 15 wherein said first polyhydroxy compound is sucrose.

17. The method of claim 15 wherein said second polyhydroxy compound comprises said first polyhydroxy compound.

18. The method of claim 50 wherein said second polyhydroxy compound differs from said first polyhydroxy compound, and said second polyhydroxy compound is substituted for said first polyhydroxy compound and said residual organic solvent in said first fraction in said dialysis step.

* * * * *